US011788985B2

(12) United States Patent
Levaray et al.

(10) Patent No.: US 11,788,985 B2
(45) Date of Patent: Oct. 17, 2023

(54) SENSING ELEMENTS COMPRISING GOLD NANOPARTICLE-GRAFTED CARBON BLACK

(71) Applicant: Stratuscent Inc., Montreal (CA)

(72) Inventors: Nicolas Levaray, Montreal (CA); Jayan Ozhikandathil, Montreal (CA); Ashok Prabhu Masilamani, Montreal (CA); Tullio Panarello, Saint-Lazare (CA)

(73) Assignee: Stratuscent Inc., Montreal (CA)

( * ) Notice: Subject to any disclaimer, the term of this patent is extended or adjusted under 35 U.S.C. 154(b) by 411 days.

(21) Appl. No.: 16/270,412

(22) Filed: Feb. 7, 2019

(65) Prior Publication Data

US 2019/0285570 A1    Sep. 19, 2019

Related U.S. Application Data

(60) Provisional application No. 62/627,533, filed on Feb. 7, 2018.

(51) Int. Cl.
*G01N 27/407* (2006.01)
*G01N 27/12* (2006.01)
(Continued)

(52) U.S. Cl.
CPC ........... *G01N 27/4071* (2013.01); *C09C 1/56* (2013.01); *G01N 27/127* (2013.01);
(Continued)

(58) Field of Classification Search
CPC .. G01N 33/0047; G01N 27/04; G01N 27/127; G01N 27/4071; C08K 3/04;
(Continued)

(56) References Cited

U.S. PATENT DOCUMENTS 6,342,295 B1    1/2002  Kobayashi
9,459,223 B1 *  10/2016 Alqahtani .......... G01N 33/0036
(Continued)

FOREIGN PATENT DOCUMENTS

GB          2560767 A       9/2018
WO    WO 2014/203923 A1    12/2014

OTHER PUBLICATIONS

A. Wong et al., Simultaneous determination of paracetamol and levofloxacin using a glassy carbon electrode modified with carbon black, silver nanoparticles and PEDOT:PSS film, Sensors and Actuators B, vol. 255, pp. 2264-2273 (2017) (Year: 2017).*
(Continued)

*Primary Examiner* — Caitlyn Mingyun Sun
(74) *Attorney, Agent, or Firm* — PIERCE ATWOOD LLP

(57) ABSTRACT

Some embodiments presented here relate to chemical sensors with enhanced sensitivity and selectivity. In an embodiment, the sensor is a composite thin film that comprises (e.g., is made of) chemically-modified carbon black and a chemically-sensitive polymer base. By grafting gold nanoparticles on carbon black, the number of binding sites on the sensor thin film is increased, thereby increasing the sensitivity. Furthermore, ligand attached gold nanoparticles are grafted on carbon black to increase the binding sites on the sensor thin film in some embodiments, which results in increased sensitivity as well as improved selectivity in some cases.

20 Claims, 11 Drawing Sheets

(51) Int. Cl.
G01N 27/04 (2006.01)
C09C 1/56 (2006.01)
G01N 33/00 (2006.01)
C08K 3/08 (2006.01)

(52) U.S. Cl.
CPC . *G01N 33/0047* (2013.01); *C08K 2003/0831* (2013.01); *G01N 27/04* (2013.01)

(58) Field of Classification Search
CPC ............ C08K 3/08; C08K 2001/0831; C08K 2201/001; C08K 2201/011; C08K 2201/0013; C08L 2203/20
See application file for complete search history.

(56) References Cited

U.S. PATENT DOCUMENTS

| | | | | |
|---|---|---|---|---|
| 2005/0142030 | A1* | 6/2005 | Kim | B82Y 15/00 422/400 |
| 2007/0114138 | A1* | 5/2007 | Krasteva | G01N 27/127 204/400 |
| 2008/0025876 | A1 | 1/2008 | Ramamurthy | |
| 2010/0276302 | A1* | 11/2010 | Raguse | G01N 27/127 427/58 |

OTHER PUBLICATIONS

M. Bron, Carbon black supported gold nanoparticles for oxygen electroreduction in acidic electrolyte solution, Journal of Electroanalytical Chemistry, vol. 624, pp. 64-68 (2008) (Year: 2008).*

A. Balamurugan, et al., Electrochemical sensing of NADH based on Meldola Blue immobilized silver nanoparticle-conducting polymer electrode, Colloids and Surfaces A: Physiochem. Eng. Aspects, vol. 362, pp. 1-7 (2010) (Year: 2010).*

F. Arduini, et al., Effective electrochemical sensor based on screen-printed electrodes modified with a carbon black-Au nanoparticles composite, Sensors and Actuators B, vol. 212, pp. 536-543 (2015) (Year: 2015).*

A. Alshammari, et al., "Supported Gold Nanoparticles as Promising Catalysts". Catalytic Application of Nano-Gold Catalysts, edited by Neeraj Mishra, pp. 57-81 (2016) (Year: 2016).*

S. Guo, et al., Platinum Nanoparticle Ensemble-on-Graphene Hybrid Nanosheet: One-Pot, Rapid Synthesis, and Used as New Electrode Material for Electrochemical Sensing, ACS Nano 2010 4 (7), 3959-3968 (Year: 2010).*

S. Demirel-Gülen, et al., Liquid phase oxidation of glycerol over carbon supported gold catalysts, Catalysis Today, vols. 102-103, pp. 166-172 (2005) (Year: 2005).*

C. Lahousse, et al., Preparation of Pd on Carbon Black by Deposition-precipitation: Study of the Effect of the Support Functionalisation. Studies in Surface Science and Catalysis. (2006) 162. pp. 601-608. (Year: 2006).*

Hebié, Seydou, et al. "Electrochemical reactivity at free and supported gold nanocatalysts surface." Catalytic Application of Nano-Gold Catalysts; Mishra, NK, Ed.; Intech: Rijeka, Croatia (2016): 101-130. (Year: 2016).*

Mallya, A.N., Kottokkaran, R. and Ramamurthy, P.C., 2014. Conducting polymer-carbon black nanocomposite sensor for volatile organic compounds and correlating sensor response by molecular dynamics. Sensors and Actuators B: Chemical, 201, pp. 308-320. (Year: 2014).*

Zhang, H.L., Evans, S.D., Henderson, J.R., Miles, R.E. and Shen, T.H., 2002. Vapour sensing using surface functionalized gold nanoparticles. Nanotechnology, 13(3), p. 439. (Year: 2002).*

International Search Report and Written Opinion for International Application No. PCT/IB2019/000471 dated Sep. 6, 2019.

Extended European Search Report dated Sep. 17, 2021 in connection with European Application No. 19755099.9.

International Preliminary Report on Patentability dated Aug. 20, 2020 in connection with International Application No. PCT/IB2019/000471.

Kim et al., Mixed-ligand nanoparticles of chlorobenzenemethanethiol and n-octanethiol as chemical sensors. Sensors and Actuators B: Chemical. Apr. 2005;106(1):189-98.

* cited by examiner

SENSING ELEMENTS COMPRISING GOLD NANOPARTICLE-GRAFTED CARBON BLACK

RELATED APPLICATIONS

This application claims priority under 35 U.S.C. § 119(e) to U.S. Provisional Application No. 62/627,533, filed Feb. 7, 2018, and entitled "A Novel Chemical Sensor Based on Gold Nanoparticles Grafted Carbon Black", which is incorporated herein by reference in its entirety for all purposes.

TECHNICAL FIELD

This invention relates generally to sensing elements, including highly sensitive and selective chemical sensors. Specifically, some embodiments of the invention comprise gold nanoparticles grafted onto carbon black in thin film composite sensors.

BACKGROUND OF THE INVENTION

Gas and Volatile Organic Compounds (VOC) sensors have become a necessity in every aspect of the modern domestic-industrial complex. In particular, real world applications like air quality monitoring, industrial monitoring, and breath-based medical diagnostics, etc. can utilize such sensors. These sensors normally operate in very complex environments with noisy backgrounds, and as such are sometimes required to meet very stringent specifications on sensitivity and specificity. There are conventional gas sensors, like electrochemical and metal oxide (MOX) sensors, that are typically used in many sensing applications. There are also catalytic and semiconductor-based gas detectors available on the market. All of these gas sensors fall under lock and key (L&K) type detectors, where each sensor is highly sensitive to only a particular analyte/gas of interest.

SUMMARY

Sensing elements, as well as related components and methods associated therewith, are generally provided.

In some embodiments, a sensing element is provided. The sensing element may comprise a polymer and carbon black. A plurality of gold nanoparticles may be grafted onto the carbon black.

In some embodiments, a sensing element comprises a polymer and carbon black. A plurality of gold nanoparticles may be grafted onto the carbon black. A plurality of ligands may be grafted onto the gold nanoparticles.

In some embodiments, a method of forming a sensing element is provided. The method may comprise depositing a mixture onto a substrate. The mixture may comprise a polymer, carbon black, and a solvent. A plurality of gold nanoparticles may be grafted onto the carbon black.

In some embodiments, a method of forming a sensing element comprises depositing a mixture onto a substrate. The mixture may comprise a polymer, carbon black, and a solvent. A plurality of gold nanoparticles may be grafted onto the carbon black. A plurality of ligands may be grafted onto the gold nanoparticles.

In some embodiments, a method of sensing an analyte is provided. The method may comprise exposing a sensing element to the analyte. The sensing element may comprise a polymer and carbon black. A plurality of gold nanoparticles may be grafted onto the carbon black.

In some embodiments, a method of sensing an analyte comprises exposing a sensing element to the analyte. The sensing element may comprise a polymer and carbon black. A plurality of gold nanoparticles may be grafted onto the carbon black. A plurality of ligands may be grafted onto the gold nanoparticles.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention is described herein by way of example with reference to different drawings (i.e., the accompanying figures), which are schematic and not intended to be drawn to scale. In the figures, the same element is represented in the same manner throughout all the drawings and each identical or nearly identical component is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
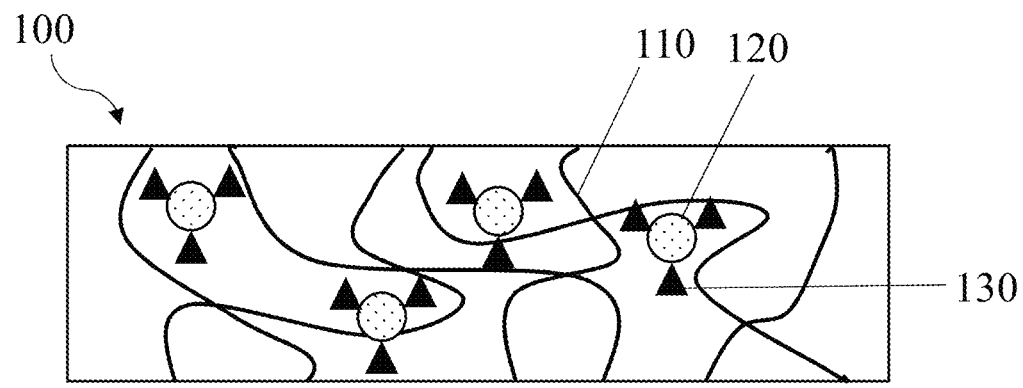
FIG. 1 is a schematic depiction of a sensing element comprising a polymer and carbon black onto which a plurality of gold nanoparticles is grafted, in accordance with some embodiments.

The following description is presented to enable the reproduction and use of the present invention. In the following description, reference is made to an embodiment or embodiments, which are meant to be interpreted broadly, and not restricted to any specific embodiment or set of specific embodiments.

Sensing elements, methods of forming sensing elements, sensors comprising sensing elements, and methods of sensing analytes (e.g., by employing sensing elements) are generally described. The sensing elements may, upon exposure to an analyte of interest, interact with the analyte of interest (e.g., the sensing elements may absorb, adsorb, and/or bind at least a portion of the analyte of interest). Interaction with the analyte of interest will typically cause the chemical composition of the sensing element to change. It may also cause the thickness of the sensing element to change and/or the microstructure of the sensing element to change. One or more of these phenomena may cause the resistivity of the sensing element to change, which may advantageously be facilely detected.

In some embodiments, a sensing element comprises a polymer, carbon black, and a plurality of gold nanoparticles. The plurality of gold nanoparticles may be grafted onto the carbon black. Some sensing elements described herein further comprise a plurality of ligands grafted onto the gold nanoparticles. Without wishing to be bound by any particular theory, it is believed that this combination of components is especially advantageous for sensing a variety of analytes. For instance, in some embodiments, a sensing element comprising the above-referenced components may be particularly sensitive to an analyte, may respond to an analyte in a manner that is facile to correlate with the concentration of the analyte, and/or may be capable of responding to an analyte in the presence of different chemical species in a relatively consistent manner. By way of example, it is believed that the presence of gold nanoparticles may enhance the sensitivity of the sensing element to a variety of analytes by increasing the number of binding sites present in the sensing element.

In some embodiments, one or more features of a component of a sensing element (e.g., one or more features of a polymer therein, carbon black therein, a gold nanoparticle therein, and/or a ligand therein) may be selected to both enhance the sensitivity of the sensing element to one or more analytes of interest. The selected component may not affect the sensitivity of the sensing element to one or more analytes not of interest, and/or may decrease the sensitivity of the sensing element to one or more analytes not of interest. This may enable the sensing element to selectively sense one or more analytes of interest without providing false positive responses to other analytes. For instance, the sensing element may comprise a particular ligand that is especially sensitive to an analyte of interest but minimally sensitive to other analytes. As another example, the sensing element may comprise a particular polymer that is particularly sensitive to an analyte of interest but minimally sensitive to other analytes. In some embodiments, a sensing element comprises a combination of polymers and/or ligands that have enhanced sensitivity to some analytes but not others. Other features of the sensing element may also be selected to enhance or reduce sensitivity of the sensing element towards particular analytes.

As described above, other types of sensors have drawbacks that some of the sensors described herein do not. While L&K sensors are effective in very targeted applications, they suffer from several limitations as follows: 1) Most of these L&K sensors suffer from cross sensitivity issues with other gases that are present in the environment or gases of the same chemical family. 2) They also suffer interference from humidity in the environment. 3) Electrochemical sensors suffer from a limited life time of 6 months and sensor stability issues. MOX sensors are among the more popular miniaturized sensors on the market, however, they need to operate at temperatures of 200° C.-300° C. with high power consumption and have corresponding temperature stability issues. There are also chemiresistive array-type sensors made of composite materials like polymer-carbon, polymer-metallic nanoparticles, conducting polymers, etc. that have been proposed for multi-gas sensing. Typically, these sensors operate based on change in conductivity due to diffusion of a gas or vapor into the composite material. However, these array devices suffer from less sensitivity (i.e., they will be able to detect a lot of analytes, but with a relative precision only when measuring analytes at the 100-1000 ppm concentration range).

Some embodiments relate to methods of forming sensing elements. A method of forming a sensing element may comprise depositing a mixture comprising one or more components to be incorporated into the sensing element onto a substrate. In some embodiments, the mixture may further comprise one or more components not to be incorporated into the sensing element (e.g., one or more volatile components configured to evaporate from the mixture during sensing element formation) and/or may lack one or more components to be incorporated into the sensing element (e.g., one or more components of the sensing element previously deposited on the substrate, one or more components of the sensing element to be deposited on the substrate subsequently). Further description of suitable methods for forming sensing elements are described in more detail below.

Some embodiments relate to methods of sensing one or more analytes. A method of sensing an analyte may comprise exposing a sensing element to an analyte. The sensing element may have one or more of the features described elsewhere herein (e.g., it may comprise one or more polymers and/or carbon black onto which one or more species are, directly and/or indirectly, grafted).

Figure 2:
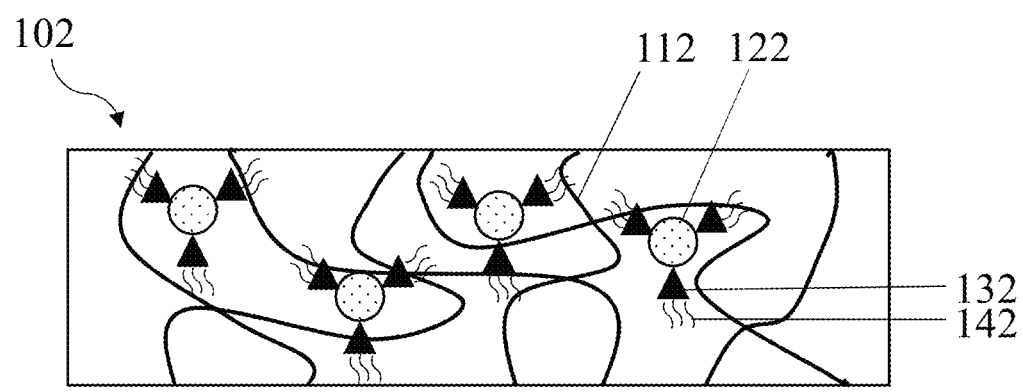
FIG. 2 is a schematic depiction of a sensing element comprising a polymer, carbon black onto which a plurality of gold nanoparticles is grafted, and a plurality of ligands grafted onto the gold nanoparticles, in accordance with some embodiments.

As described above, some embodiments relate to sensing elements comprising a polymer and carbon black onto which a plurality of gold nanoparticles are grafted. FIG. 1 shows one non-limiting embodiment of a sensing element 100 comprising a polymer 110, carbon black 120, and a plurality of gold nanoparticles 130 grafted onto the carbon black. FIG. 2 shows another non-limiting embodiment of a sensing element. In FIG. 2, a sensing element 102 comprises a polymer 102, carbon black 122, a plurality of gold nanoparticles 132 grafted onto the carbon black, and a plurality of ligands 142 grafted onto the gold nanoparticles. It should be understood that FIGS. 1 and 2 are purely schematic, and that some embodiments may differ from the sensing elements shown in FIGS. 1 and 2 in one or more ways. For instance, some sensing elements may comprise further components (e.g., one or more surfactants, a second polymer different than the polymer shown in FIGS. 1 and 2) and/or may include the components shown in FIGS. 1 and 2 in different relative amounts (e.g., some sensing elements may have a relatively higher amount of polymer in comparison to carbon black than shown in FIGS. 1 and 2, and/or may have a relatively higher density of ligands grafted onto the plurality of gold nanoparticles than shown in FIG. 2). It should also be understood that the shapes and sizes of the components shown in FIGS. 1 and 2 are purely exemplary, and that some sensing elements may comprise polymers, carbon black, gold nanoparticles, and/or ligands having different relative sizes than shown in FIGS. 1 and 2.

In some embodiments, like the embodiments shown in FIGS. 1 and 2, a sensing element comprises a polymer and carbon black, and the carbon black and any species grafted thereonto are dispersed in a matrix formed by the polymer. The carbon black and the species grafted thereonto may be relatively well-dispersed. For instance, in some embodiments, the carbon black and the species grafted thereonto do not form any aggregates visible by eye and/or may not form any aggregates visible by optical microscope. In some embodiments, a relatively minor percentage of the carbon black and the species grafted thereonto may form aggregates. By way of example, less than 20%, less than 10%, less than 5%, less than 2%, or less than 1% of the carbon black particles may be aggregated.

In some embodiments, carbon black and any species grafted thereonto are positioned relatively uniformly throughout a matrix formed by the polymer. For instance, in some embodiments, the carbon black and the species grafted thereonto may be dispersed such that the density of the carbon black and the species grafted thereonto is relatively uniform throughout the matrix formed by the polymer. By way of example, the density of the carbon black and the species grafted thereonto may vary by less than 20%, less than 10%, less than 5%, less than 2%, or less than 1% throughout the matrix formed by the polymer.

It should also be understood that some embodiments relate to arrangements of polymers, carbon black, gold nanoparticles, and/or ligands other than those shown in FIGS. 1 and 2. For instance, in some embodiments, the carbon black and any species grafted thereonto may form a percolating network through the sensing element. As another example, the carbon black and any species grafted thereonto may make up a volume fraction of the sensing element other than that shown in FIGS. 1 and 2. As a third example, the carbon black and any species grafted thereonto may have a size relative to the thickness of the sensing element other than that shown in FIGS. 1 and 2. As a fourth example, the relative sizes of the carbon black and the components grafted thereonto may be different than that shown in FIGS. 1 and 2 (e.g., the gold nanoparticles may have a different size relative to the carbon black than shown in FIGS. 1 and 2, and/or the ligands may have a different size relative to the gold nanoparticles than shown in FIG. 2). As a fifth example, the relative amounts of the carbon black, gold nanoparticles, and/or ligands may be different than those shown in FIGS. 1 and 2. Further differences from the sensing elements shown in FIGS. 1 and 2 are also contemplated.

The sensing elements described herein, such as those shown in FIGS. 1 and 2, may have a variety of suitable shapes. In some embodiments, the sensing element forms a shape that has a circular cross-section parallel to a substrate on which it is disposed. The cross-section may have a shape that is approximately, but not perfectly, circular. For instance, the cross-section of the sensing element may have a shape for which a circle can be drawn that overlaps with greater than or equal to 95%, greater than or equal to 97.5%, greater than or equal to 99%, greater than or equal to 99.5%, or greater than or equal to 99.9% of the cross-section of the sensing element. The cross-section of the sensing element may have a shape for which a circle can be drawn that overlaps with less than or equal to 100%, less than or equal to 99.9%, less than or equal to 99.5%, less than or equal to 99%, or less than or equal to 97.5% of the cross-section of the sensing element. Combinations of the above-referenced ranges are also possible (e.g., greater than or equal to 95% and less than or equal to 100%). Other ranges are also possible.

Figure 3:
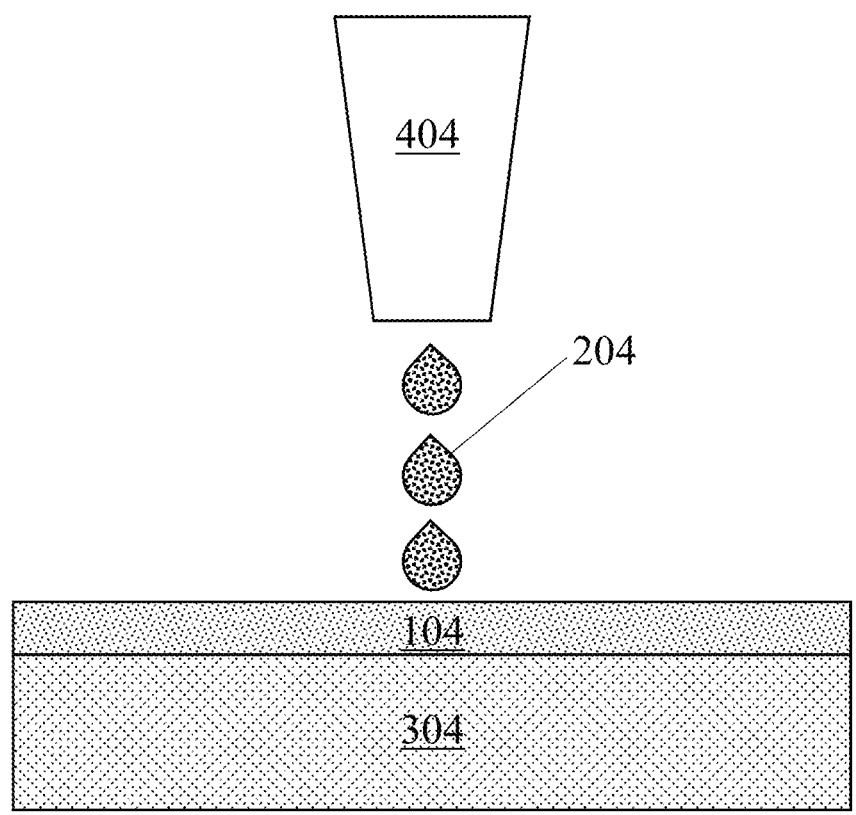
FIG. 3 shows a method of fabricating a sensing element, in accordance with some embodiments.

As described above, some embodiments relate to methods of forming sensing elements. FIG. 3 shows one non-limiting embodiment of a method of forming a sensing element. In FIG. 3, a mixture 204 is deposited onto a substrate 304 to form a sensing element 104. The mixture may comprise components to be included in the sensing element (e.g., one or more polymers, carbon black, a plurality of gold nanoparticles grafted to the carbon black, and/or a plurality of ligands grafted to the gold nanoparticles) and may further comprise components not to be included in the sensing element (e.g., one or more volatile solvents). In FIG. 3, the mixture 204 is deposited from a nozzle 404 in the form of droplets that spread on the substrate 304 to form the sensing element 104. In some embodiments, a procedure similar to the one in FIG. 3 is employed (e.g., a liquid mixture comprising the relevant components may be deposited in the form of droplets from a nozzle onto a substrate to form a sensing element). However, it is also possible for a method of forming a sensing element to differ from the method shown in FIG. 3 in one or more ways. For instance, a liquid mixture may be deposited onto a substrate in the form of a liquid jet, a mixture may be deposited onto a substrate from more than one nozzle, and/or a mixture may be deposited onto a substrate in a manner other than from a nozzle (e.g., a mixture may be poured onto the substrate).

It should also be understood that some methods may comprise additional steps beyond those shown in FIG. 3. For instance, some methods may comprise steps related to forming the mixture. In some embodiments, a method comprises combining two or more of the components of the mixture (e.g., a solvent, one or more polymers, carbon black, a plurality of gold nanoparticles grafted to the carbon black, and/or a plurality of ligands grafted to the gold nanoparticles). The components of the mixture may be mixed to form the mixture (e.g., after being combined). By way of example, in some embodiments, the mixture may be subject to vibrations, such as ultrasonic vibrations, to aid mixing thereof (e.g., by placement in an ultrasonic bath, by use of an ultrasonic stick). In some embodiments, a method comprises a step of waiting after the formation of a mixture prior to deposition of the mixture onto the substrate. In some embodiments, a method comprises one or more steps taking place after the deposition of a mixture onto a substrate. By way of example, a method may comprise heating the deposited mixture. In other words, a method may comprise depositing a mixture onto a substrate, and then heating the materials deposited onto the substrate from the mixture (e.g., the non-volatile components of the mixture).

In some embodiments, a deposited mixture is heated by heating the substrate onto which it is deposited. The deposited mixture may be heated to a variety of suitable temperatures. For instance, in some embodiments, a deposited mixture is heated to a temperature of greater than or equal to 40° C., greater than or equal to 42.5° C., greater than or equal to 45° C., greater than or equal to 47.5° C., greater than or equal to 50° C., greater than or equal to 52.5° C., greater than or equal to 55° C., or greater than or equal to 57.5° C. In some embodiments, a deposited mixture is heated to a temperature of less than or equal to 60° C., less than or equal to 57.5° C., less than or equal to 55° C., less than or equal to 52.5° C., less than or equal to 50° C., less than or equal to 47.5° C., less than or equal to 45° C., or less than or equal to 42.5° C. Combinations of the above-referenced ranges are also possible (e.g., greater than or equal to 40° C. and less than or equal to 60° C.). Other ranges are also possible.

A variety of suitable types of mixtures may be employed to form the sensing elements described herein. For instance, the mixture may be a solution, a suspension, a colloid, or any other suitable type of mixture. The mixture may be relatively uniform throughout its volume (e.g., the density of the components thereof may be relatively constant throughout the mixture, the mixture may be a homogeneous mixture), or the mixture may vary throughout its volume (e.g., the density of one or more components thereof may vary across its volume, the mixture may be a heterogeneous mixture).

Some embodiments relate to sensors, such as chemical sensors, comprising the sensing elements described herein. Sensors may comprise, in addition to a sensing element, one or more additional components. These may include electrodes, electrical circuitry (e.g., sampling circuitry, signal processing circuitry), electrical connectors, and/or enclosures. In some embodiments, a sensor comprises a sensing element and a plurality of electrodes, and the plurality of electrodes is configured to sense a change in a resistivity of the sensing element upon exposure to an analyte. By way of example, a voltage may be applied across the sensing element by the plurality of electrodes, and the resultant current may be measured as a function of time. Changes in the resultant current upon exposure of the sensing element to the analyte may be detected.

When a sensor comprises both a sensing element and an electrode, the sensing element may cover an appreciable area fraction of the electrode. In some embodiments, a sensing element disposed on an electrode covers greater than or equal to 95%, greater than or equal to 97.5%, greater than or equal to 99%, greater than or equal to 99.5%, or greater than or equal to 99.9% of the area of the electrode. A sensing element disposed on an electrode may cover less than or equal to 100%, less than or equal to 99.9%, less than or equal to 99.5%, less than or equal to 99%, or less than or equal to 97.5% of the area of the electrode. Combinations of the above-referenced ranges are also possible (e.g., greater than or equal to 95% and less than or equal to 100%). Other ranges are also possible.

Some embodiments relate to pluralities of sensors. Each sensor in a plurality of sensors may be alike, each sensor in a plurality of sensors may differ from the other sensors in one or more ways (e.g., each sensor in the plurality of sensors may comprise a different sensing element), or some sensors in the plurality of sensors may be alike and some may differ from the other sensors in one or more ways (e.g., some sensors in the plurality of sensors may comprise sensing elements that are alike, and some sensors in the plurality of sensors may comprise different sensing elements from other sensors in the plurality of sensors).

Pluralities of sensors described herein may be spaced with respect to each other in a variety of suitable manners. In some embodiments, a plurality of sensors is spaced with respect to each other in an ordered, repeating manner. For instance, the plurality of sensors may be positioned such that they form a repeating lattice structure, or may be spaced with respect to each other such that a repeating lattice structure can be drawn for which the standard deviation of the distance between the sensors and the lattice points is relatively small (e.g., less than or equal to 5% of the distance between the lattice points, less than or equal to 2.5% of the distance between the lattice points, less than or equal to 1% of the distance between the lattice points, less than or equal to 0.5% of the distance between the lattice points, or less than or equal to 0.1% of the distance between the lattice points). The relevant lattice may have a variety of symmetries. In some embodiments, the lattice is a rectangular lattice and/or a square lattice.

Pluralities of sensors may be spaced with respect to each other at a variety of suitable distances. In some embodiments, a plurality of sensors is spaced such that a repeat distance between the sensors is greater than or equal to 2 mm, greater than or equal to 2.25 mm, greater than or equal to 2.5 mm, greater than or equal to 2.75 mm, greater than or equal to 3 mm, greater than or equal to 3.5 mm, greater than or equal to 4 mm, or greater than or equal to 4.5 mm. In some embodiments, a plurality of sensors is spaced such that a repeat distance between the sensors is less than or equal to 5 mm, less than or equal to 4.5 mm, less than or equal to 4 mm, less than or equal to 3.5 mm, less than or equal to 3 mm, less than or equal to 2.75 mm, less than or equal to 2.5 mm, or less than or equal to 2.25 mm. Combinations of the above-referenced ranges are also possible (e.g., greater than or equal to 2 mm and less than or equal to 2.5 mm, greater than or equal to 2 mm and less than or equal to 3 mm, or greater than or equal to 2 mm and less than or equal to 5 mm). It should be understood that some pluralities of sensors may be spaced with respect to each other such that there are two repeat distances (e.g., in the case of a plurality of sensors forming a rectangular array). For such embodiments, each repeat distance may independently be within one or more of the ranges listed above.

Figure 4A:
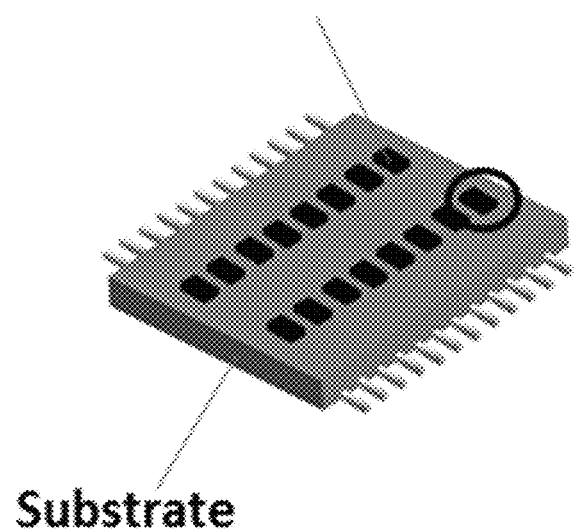
FIG. 4a illustrates the thin film sensor array on a substrate, in accordance with some embodiments.
Figure 4B:
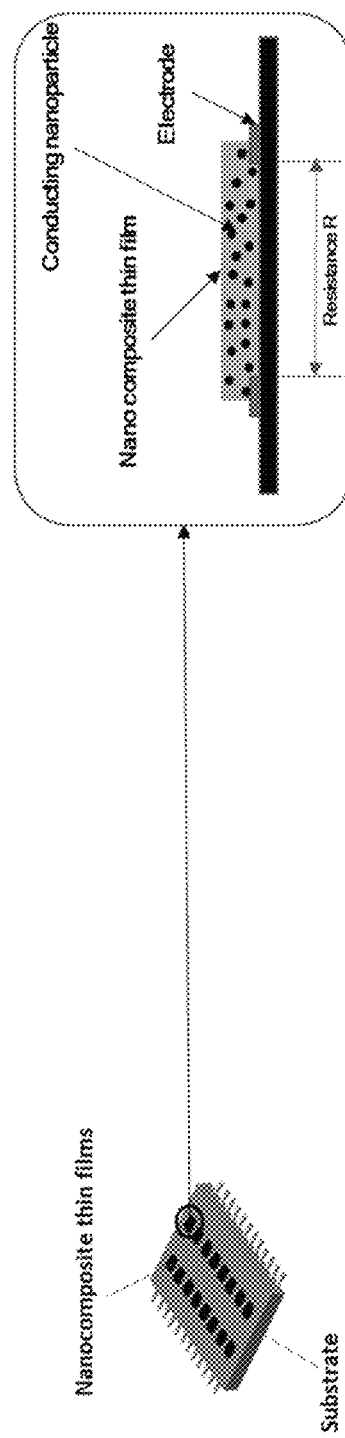
FIG. 4b illustrates one of the composite thin film sensors, in accordance with some embodiments.

The sensors, and/or chemical sensors, and/or gas sensors described in this disclosure may represent and/or be components of physical devices comprising an array of thin films deposited on top of a substrate (FIG. 4a). In some embodiments, each element in the array (e.g., each sensing element) is made of a chemically-sensitive thin film which contains a composite material embedded with conducting nanoparticles (FIG. 4b). In some embodiments, as described elsewhere herein, a sensor (e.g., a chemical sensor and/or a gas sensor) comprises a sensing element (e.g., a sensing element comprising a polymer, carbon black, a plurality of gold nanoparticles grafted onto the carbon black, and/or a plurality of ligands grafted onto the gold nanoparticles). One or more sensing elements may take the form of a film, such as a thin film.

Figure 5A:
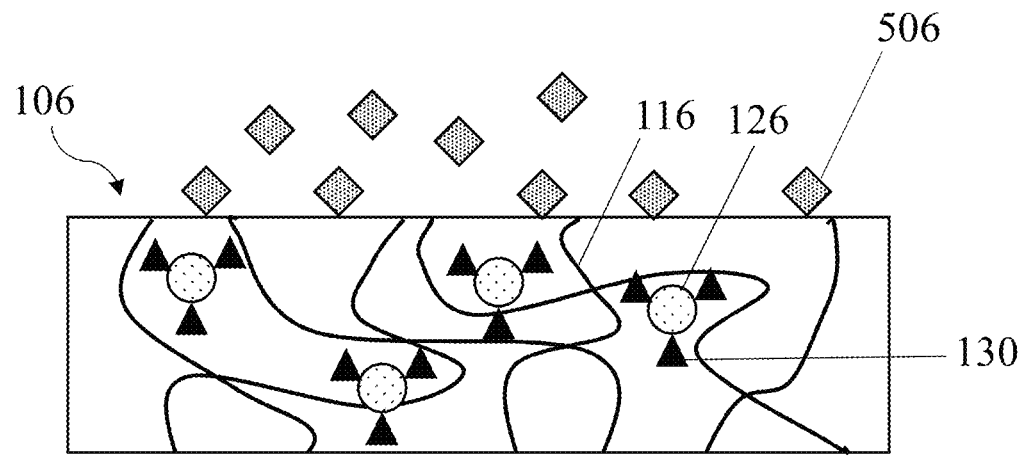
FIGS. 5a-5b show a method of exposing a sensing element to an analyte, in accordance with some embodiments.
Figure 5B:
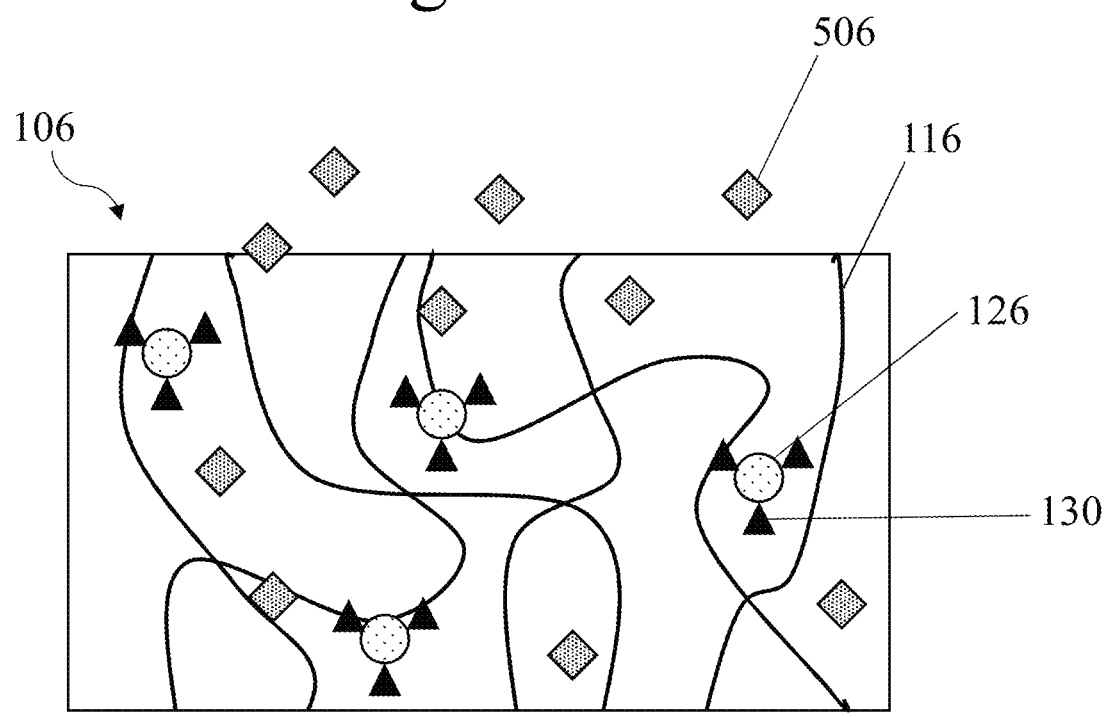

Some embodiments may relate to methods of exposing a sensing element (and/or a sensor comprising a sensing element) to an analyte and/or relate to sensing elements (and/or sensors comprising sensing elements) configured to undergo a detectable change upon exposure to an analyte. FIGS. 5a and 5b show one non-limiting embodiment of a method of doing so. In FIG. 5a, a sensing element 106 comprising a polymer 116 and carbon black 126 onto which a plurality 130 of gold nanoparticles is grafted is exposed to an analyte 506. As shown in FIG. 5b, the sensing element may interact with an analyte to which it is exposed (e.g., the sensing element may at least partially absorb, adsorb, and/or bind the analyte). As also shown in FIG. 5b, the sensing element may increase in thickness upon interaction with an analyte and/or the spacing between the carbon black in the sensing element may increase upon interaction of the sensing element with the analyte. Without wishing to be bound by any particular theory, and as described in further detail below, one or both of these changes may increase the resistivity of the sensing element to a measurable degree. Accordingly, exposing a sensing element to an analyte may cause a measurable change in a property of the analyte, which may allow the analyte to be sensed.

It should be understood that some sensing elements may not interact with some analytes, or may interact with some analytes to a relatively low degree. For such pairs of sensing elements and analytes, the thickness of the sensing element, spacing between the carbon black in the sensing element, and/or resistivity of the sensing element may change not at all or little upon exposure of the sensing element to the analyte.

Additionally, it should be understood that, although FIGS. 5a and 5b show interaction between a single analyte and a sensing element lacking a plurality of ligands, some embodiments may relate to exposing a sensing element comprising a plurality of ligands grafted onto a plurality of gold nanoparticles and/or to exposing a sensing element to more than one analyte at a time. In such embodiments, the sensing element may interact with all, some, or none of the analytes to which it is exposed. It should also be understood that embodiments may relate to exposing any of the sensing elements described herein (and/or sensing elements having one or more of the features described herein) to one or more analytes.

Exposure of a sensing element to an analyte may take a variety of suitable forms, but typically comprises positioning the sensing element may be positioned in an environment in which the analyte is present and/or introducing an analyte into an environment in which the sensing element is present. In some embodiments, exposing a sensing element to an analyte comprises directly contacting the analyte with the sensing element. Directly contacting the analyte with the sensing element may comprise, for instance, contacting a fluid comprising the analyte with the sensing element, as described in more detail below.

Figure 4C:
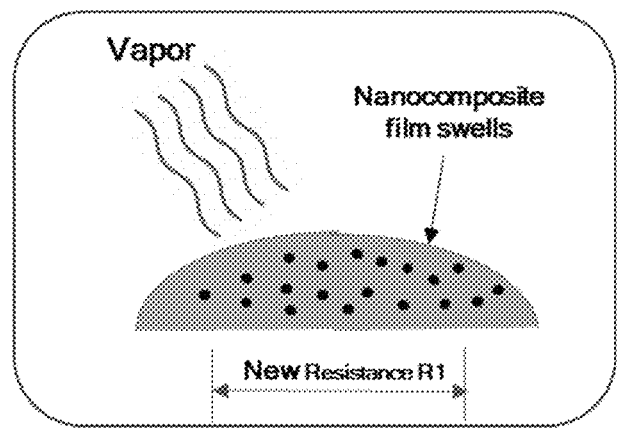
FIG. 4c illustrates one of the sensing mechanisms of the thin film sensor, in accordance with some embodiments.

Upon exposure to a molecule or a combination of molecules, which could be in a liquid state and/or in a vapor state (which may be referred to by the words analytes, gas and/or VOCs in the previous and following description), a sensing element (e.g., the thin film) may be subject to and/or undergo a detectable change, such as a physical change. These physical changes may include but are not limited to swelling (FIG. 4c), contracting, or staying in the same state. Stated differently, a sensing element may increase in thickness, decrease in thickness, or exhibit no change in thickness when exposed to an analyte. The sensing element may exhibit a change in one or more physical properties other than thickness, such as electrical resistivity, concurrently or instead of exhibiting a change in thickness. The physical change(s) exhibited by the sensing element may be capable of being monitored. By way of example, a change in the electrical response from the thin film (FIG. 4c), such as a change in the electrical response of the sensing element due to interaction with an analyte and/or due to a change in the thickness of the sensing element upon exposure to an analyte, may be measurable.

Figure 4D:
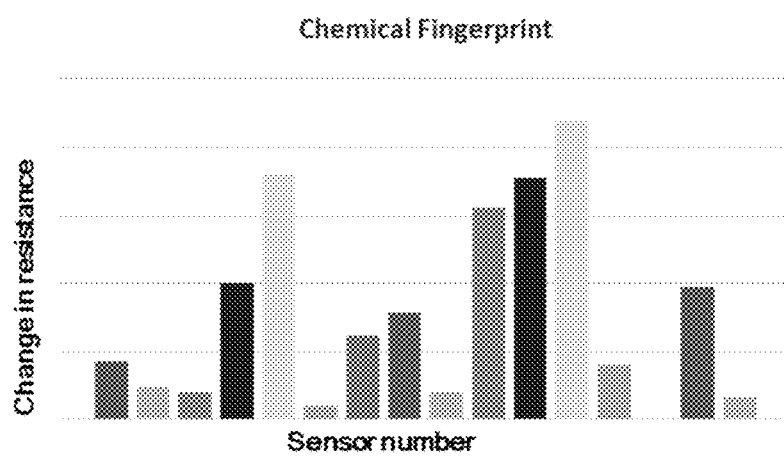
FIG. 4d is the graphical representation of the response across the sensor array upon exposure of the sensor array to an analyte, in accordance with some embodiments.

In some embodiments, the change in electrical response across an array of sensing elements (e.g., across the array of thin films) can be measured (FIG. 4d). The resulting pattern of change in electrical response may represent the "fingerprint" of the exposed analyte. Advantageously, different analytes may have differing fingerprints (e.g., a first analyte may cause an array of sensing elements to have a first set of electrical responses, and a second analyte may cause an array of sensing elements to have a second, different, set of electrical responses). This may desirably allow for identification of an analyte based on its fingerprint.

The sensing element may respond to the analyte in a manner that changes with time, in a manner that is relatively constant over time, or in a manner that initially changes with time but then reaches a steady state value. For instance, in some embodiments, a sensing element is first exposed to an analyte and begins to interact with the analyte (e.g., by absorption, adsorption, and/or binding). As the sensing element begins to interact with the analyte, it may begin to undergo one or more structural, compositional, and/or electrical changes as described elsewhere herein. After interacting with the analyte for a period of time, the sensing element may reach an equilibrium with the analyte. In other words, it may absorb, adsorb, and/or bind a sufficient amount of the analyte such that it is in chemical equilibrium (e.g., a dynamic equilibrium) with the environment to which it is exposed. At this point in time, the sensing element may interact with the analyte in a relatively constant manner (e.g., without undergoing significant changes in the amount of analyte absorbed therein, adsorbed thereon, and/or bound thereto) and may exhibit relatively constant structural, compositional, and/or electrical properties. If the environment to which the sensing element is exposed changes such that the amount of analyte therein is changed (e.g., increased, decreased), the sensing element may again begin to respond to the analyte in a manner that changes over time. For instance, in the case of an environment comprising a lower amount of analyte, the sensing element may desorb and/or debind analyte therefrom. This may cause the sensing element to again undergo one or more structural, compositional, and/or electrical changes (e.g., the sensing element may return to a structure and/or composition it had prior to exposure to the analyte, the sensing element may exhibit the resistivity it exhibited prior to exposure to the analyte). Absent explicit indication to the contrary, references to interaction of a sensing element with an analyte may refer to interaction of the sensing element with the analyte at any point in time (e.g., during initial exposure, during steady state exposure, etc.).

Some embodiments of the present disclosure relate to the chemistry aspect of the thin film chemical sensor. Stated differently, some embodiments relate to sensing elements comprising a combination of components that are particularly beneficial. This disclosure describes, among other features, a new design for the composition of the chemical sensor (e.g., for a sensing element positioned in a chemical sensor) and/or of the sensor array. A typical chemical sensor is made of a conductive material and a sensing material (FIG. 4b). The conductive material typically decreases the electrical resistivity of the sensing element, and the sensing material is typically a material that is configured to interact with an analyte of interest (e.g., it may be a material configured to absorb, adsorb, and/or bind at least a portion of the analyte of interest). However, with adequate chemical modifications the conductive material can be part of the sensing process thereby increasing the sensitivity of the sensor. In other words, some embodiments relate to sensing elements comprising one or more components that are both electrically conductive and configured to interact with one or more analytes of interest (e.g., by absorption, adsorption, and/or binding). Further description of specific components that may be included in sensing elements are described in further detail below.

As described above, in some embodiments, a sensing element comprises carbon black (CB). As described in further detail elsewhere herein, the carbon black may be chemically-modified in order to enhance its sensitivity to one or more analytes. In other words, the basic conductive material used for chemical modification to improve sensitivity is carbon black in some embodiments. Carbon black typically comprises incomplete combustion products of one or more organic materials. It may comprise elemental carbon, and may have a variety of morphologies (e.g., it may be partially amorphous and/or it may comprise one or more regions that are microcrystalline).

In some embodiments, a sensing element comprises carbon black that takes the form of a plurality of particles comprising carbon black. The carbon black particles may advantageously have a relatively high surface area, which may allow for a relatively large amount of other desirable species (e.g., species that enhance the sensitivity of the sensing element to one or more analytes, such as gold nanoparticles) to be grafted thereto.

In some embodiments, a sensing element comprises carbon black that has a relatively low resistivity. The carbon black may have a resistivity of less than or equal to 200 kOhms, less than or equal to 175 kOhms, less than or equal to 150 kOhms, less than or equal to 125 kOhms, less than or equal to 100 kOhms, less than or equal to 75 kOhms, less than or equal to 50 kOhms, less than or equal to 40 kOhms, or less than or equal to 30 kOhms. The carbon black may have a resistivity of greater than or equal to 20 kOhms, greater than or equal to 30 kOhms, greater than or equal to 40 kOhms, greater than or equal to 50 kOhms, greater than or equal to 75 kOhms, greater than or equal to 100 kOhms, greater than or equal to 125 kOhms, greater than or equal to 150 kOhms, or greater than or equal to 175 kOhms. Combinations of the above-referenced ranges are also possible (e.g., greater than or equal to 20 kOhms and less than or equal to 200 kOhms). Other ranges are also possible.

Figure 6A:
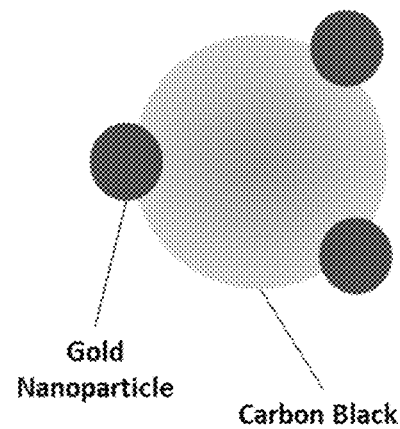
FIG. 6a illustrates carbon black grafted with gold nanoparticles, in accordance with some embodiments.

As described elsewhere herein, in some embodiments related to one or more inventions described herein, carbon black is chemically processed to produce "gold nanoparticles (AuNps) grafted carbon black (CB)" which hereafter will be referred as CB-AuNp (FIG. 6a). In other words, some embodiments relate to sensing elements comprising carbon black onto which a plurality of gold nanoparticles are grafted. As described above, the presence of a plurality of gold nanoparticles may advantageously enhance the sensitivity of the sensing element to a variety of analytes. The plurality of gold nanoparticles may be grafted onto the carbon black in a variety of suitable manners. For instance, in some embodiments, gold nanoparticles grafted onto the carbon black are attached thereto via a chemical bond. The chemical bond may be an organometallic bond and/or a covalent bond. Gold nanoparticles grafted onto carbon black may be grafted thereonto such that they are stably attached to the carbon black. By way of example, the gold nanoparticles may remain grafted onto the carbon black when the sensing element is exposed to one or more analytes, when its exposure to one or more analytes is terminated, and/or throughout the lifetime of the sensing element. In some embodiments, gold nanoparticles grafted onto carbon black remain attached thereto absent one or more harsh conditions designed to remove the gold nanoparticles from the carbon black (e.g., high temperatures, harsh reagents, strong oxidants).

When present, the gold nanoparticles comprise gold, and may also comprise one or more further species in addition to the gold. The other species may comprise one or more contaminants (e.g., one or more contaminants introduced into the gold nanoparticles during synthesis thereof), and/or may comprise one or more species that are not contaminants (e.g., one or more species intentionally introduced into the gold nanoparticles). These further species may include small molecules and/or other species present at a portion or all of the surface of the gold nanoparticles. In some embodiments, the gold nanoparticles comprise a relatively high amount of gold. For instance, gold may make up greater than or equal to 50 wt %, greater than or equal to 75 wt %, greater than or equal to 90 wt %, greater than or equal to 95 wt %, greater than or equal to 97.5 wt %, greater than or equal to 99 wt %, greater than or equal to 99.9 wt %, or greater than or equal to 99.99 wt % of the gold nanoparticles. In some embodiments, gold makes up less than or equal to 100 wt %, less than or equal to 99.99 wt %, less than or equal to 99.9 wt %, less than or equal to 99 wt %, less than or equal to 97.5 wt %, less than or equal to 95 wt %, less than or equal to 90 wt %, or less than or equal to 75 wt % of the gold nanoparticles. Combinations of the above-referenced ranges are also possible (e.g., greater than or equal to 50 wt % and less than or equal to 100 wt %). Other ranges are also possible.

When present, the gold nanoparticles may have a variety of suitable average diameters. In some embodiments, a sensing element comprises a plurality of gold nanoparticles having an average diameter of greater than or equal to 2 nm, greater than or equal to 5 nm, greater than or equal to 7.5 nm, greater than or equal to 10 nm, greater than or equal to 15 nm, greater than or equal to 20 nm, greater than or equal to 25 nm, greater than or equal to 30 nm, greater than or equal to 35 nm, greater than or equal to 40 nm, or greater than or equal to 45 nm. In some embodiments, a sensing element comprises a plurality of gold nanoparticles having an average diameter of less than or equal to 50 nm, less than or equal to 45 nm, less than or equal to 40 nm, less than or equal to 35 nm, less than or equal to 30 nm, less than or equal to 25 nm, less than or equal to 20 nm, less than or equal to 15 nm, less than or equal to 10 nm, less than or equal to 7.5 nm, or less than or equal to 5 nm. Combinations of the above-referenced ranges are also possible (e.g., greater than or equal to 2 nm and less than or equal to 50 nm). Other ranges are also possible. The average diameter may be determined by transmission electron microscopy. As used herein, the average diameter of the gold nanoparticles refers to the number average diameter of the gold nanoparticles (i.e., the number average of the diameters of the gold nanoparticles). The diameter of each gold nanoparticle is equivalent to the diameter of a spherical gold nanoparticle having an equivalent volume to that gold nanoparticle.

In some embodiments, a sensing element comprises a plurality of gold nanoparticles grafted onto carbon black, and the ratio of the weight of the gold nanoparticles to the weight of the carbon black has a particularly advantageous value. For instance, the ratio of the weight of the gold nanoparticles to the weight of the carbon black may be greater than or equal to 0.001, greater than or equal to 0.002, greater than or equal to 0.005, greater than or equal to 0.0075, greater than or equal to 0.01, greater than or equal to 0.02, greater than or equal to 0.05, greater than or equal to 0.075, greater than or equal to 0.1, greater than or equal to 0.15, greater than or equal to 0.2, greater than or equal to 0.25, greater than or equal to 0.3, greater than or equal to 0.4, greater than or equal to 0.5, greater than or equal to 0.6, or greater than or equal to 0.8. The ratio of the weight of the gold nanoparticles to the weight of the carbon black may be less than or equal to 1, less than or equal to 0.8, less than or equal to 0.6, less than or equal to 0.5, less than or equal to 0.4, less than or equal to 0.3, less than or equal to 0.25, less than or equal to 0.2, less than or equal to 0.15, less than or equal to 0.1, less than or equal to 0.075, less than or equal to 0.05, less than or equal to 0.02, less than or equal to 0.01, less than or equal to 0.0075, less than or equal to 0.005, or less than or equal to 0.002. Combinations of the above-referenced ranges are also possible (e.g., greater than or equal to 0.001 and less than or equal to 0.5). Other ranges are also possible.

Figure 6B:
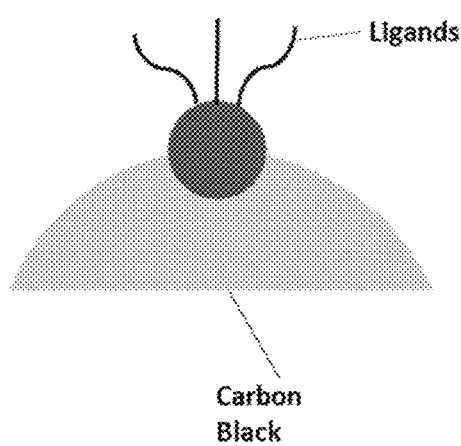
FIG. 6b illustrates carbon black grafted with ligand-attached gold nanoparticles, in accordance with some embodiments.
Figure 6C:
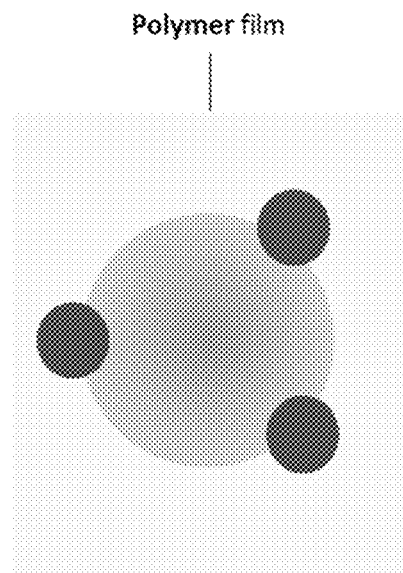
FIG. 6c illustrates carbon black grafted with gold nanoparticles embedded in a polymer matrix, in accordance with some embodiments.

As described above, in some embodiments, a sensing element comprises a plurality of gold nanoparticles grafted onto carbon black and a plurality of ligands grafted onto the gold nanoparticles. The carbon black, gold nanoparticles grafted thereonto, and ligands grafted thereonto together may be referred to as "ligand attached CB-AuNp" and/or CB-AuNp-L (FIG. 6b). As described above, the presence of a plurality of ligands may advantageously enhance the sensitivity of the sensing element to one or more analytes. In some embodiments, this enhancement may be selective. In other words, the plurality of ligands may enhance the sensitivity of the sensing element to some analytes while not affecting its sensitivity (or decreasing its sensitivity) to others. Such ligands may cause the sensing element to respond strongly to some analytes and respond weakly or not at all to others. This phenomenon may desirably allow the output from the sensing element to be different for different analytes, allowing for analytes to be distinguished more easily.

When present, the plurality of ligands may be grafted onto the plurality of gold nanoparticles in a variety of suitable manners. For instance, in some embodiments, ligands grafted onto the gold nanoparticles are attached thereto via a chemical bond. The chemical bond may be an organometallic bond and/or a covalent bond. Ligands grafted onto gold nanoparticles may be grafted thereonto such that they are stably attached to the gold nanoparticles. By way of example, the ligands may remain grafted onto the gold nanoparticles when the sensing element is exposed to one or more analytes, when its exposure to one or more analytes is terminated, and/or throughout the lifetime of the sensing element. In some embodiments, ligands grafted onto gold nanoparticles remain attached thereto absent one or more harsh conditions designed to remove the ligands from the gold nanoparticles (e.g., high temperatures, harsh reagents, strong oxidants).

In some embodiments, a relatively large number of ligands may be grafted onto a plurality of gold nanoparticles. For instance, in some embodiments, a plurality of ligands grafted onto a surface of the plurality of gold nanoparticles fully saturates the surface of the gold nanoparticles. In other words, in some embodiments, a plurality of ligands may be grafted onto a plurality of gold nanoparticles at the maximum possible density. In some embodiments, a plurality of ligands is grafted onto a plurality of gold nanoparticles at a density of greater than or equal to 50%, greater than or equal to 75%, greater than or equal to 90%, greater than or equal to 95%, greater than or equal to 97.5%, greater than or equal to 99%, greater than or equal to 99.9%, or greater than or equal to 99.99% of the maximum possible grafting density. In some embodiments, a plurality of ligands is grafted onto a plurality of gold nanoparticles at a density of less than or equal to 100%, less than or equal to 99.99%, less than or equal to 99.9%, less than or equal to 99%, less than or equal to 97.5%, less than or equal to 95%, less than or equal to 90%, or less than or equal to 75% of the maximum possible grafting density. Combinations of the above-referenced ranges are also possible (e.g., greater than or equal to 50% and less than or equal to 100%). Other ranges are also possible.

A variety of suitable ligands may be grafted onto a plurality of gold nanoparticles. In some embodiments, a ligand comprises a functional group bonded to the gold nanoparticle, such as a thiolate group, a thiophene group, and/or an acidic group. The ligand may further comprise one or more further functional groups configured to interact with one or more analytes of interest, such as acidic functional groups (e.g., carboxylic acids), amines (e.g., secondary amines, tertiary amines), alcohols (e.g., phenol functional groups), aromatic functional groups (e.g., phenyl functional groups, phenol functional groups, fluorobenzyl functional groups), fluorinated functional groups (e.g., fluorinated alkyl chains, fluorobenzyl functional groups), furans, and alkyl functional groups. In some embodiments, a ligand comprises two or more of the above-referenced functional groups (e.g., in addition to the functional group bonded to the gold nanoparticle). By way of example, a ligand may comprise an alkyl chain connecting a thiolate group with a fluorinated functional group, a carboxylic acid functional group, an amine, or a phenyl ring.

When a ligand comprises a fluorinated or unfluorinated alkyl chain, the fluorinated or unfluorinated alkyl chain may have a variety of suitable lengths. For instance, a ligand may comprise a fluorinated or unfluorinated alkyl chain having a length of greater than or equal to 1 carbon, greater than or equal to 2 carbons, greater than or equal to 3 carbons, greater than or equal to 4 carbons, greater than or equal to 5 carbons, greater than or equal to 6 carbons, greater than or equal to 7 carbons, greater than or equal to 8 carbons, greater than or equal to 9 carbons, greater than or equal to 10 carbons, greater than or equal to 11 carbons, greater than or equal to 12 carbons, greater than or equal to 13 carbons, greater than or equal to 14 carbons, greater than or equal to 15 carbons, greater than or equal to 16 carbons, greater than or equal to 17 carbons, greater than or equal to 18 carbons, or greater than or equal to 19 carbons. A ligand may comprise a fluorinated or unfluorinated alkyl chain having a length of less than or equal to 20 carbons, less than or equal to 19 carbons, less than or equal to 18 carbons, less than or equal to 17 carbons, less than or equal to 16 carbons, less than or equal to 15 carbons, less than or equal to 14 carbons, less than or equal to 13 carbons, less than or equal to 12 carbons, less than or equal to 11 carbons, less than or equal to 10 carbons, less than or equal to 9 carbons, less than or equal to 8 carbons, less than or equal to 7 carbons, less than or equal to 6 carbons, less than or equal to 5 carbons, less than or equal to 4 carbons, less than or equal to 3 carbons, or less than or equal to 2 carbons. Combinations of the above-referenced ranges are also possible (e.g., greater than or equal to 1 carbon and less than or equal to 20 carbons).

If an alkyl chain is fluorinated, it may be fully fluorinated (i.e., each carbon may be bonded only to other carbons and to fluorine atoms) or partially fluorinated (i.e., the alkyl chain may be bonded to carbon atoms, fluorine atoms, and atoms other than carbon and fluorine). If partially fluorinated, the fluorine atoms may be uniformly distributed along the alkyl chain, or some portions of the alkyl chain may be enriched in fluorine in comparison to other portions of the alkyl chain.

Non-limiting examples of suitable ligands include trifluorobutanethiolate, 4-sulfanylbutanoate, 3-aminopropane-1-thiolate, 2-phenylethanethiolate, 4-hydroxythiophenolate, furanyl-2-methanethiolate, p-fluorotoluene-alpha-thiolate, 1-decanethiolate, 1-octadecanethiolate, 3,3,4,4,5,5,6,6,7,7,8,8,8-trideclafluoro-1-octanethiolate, and 3,3,4,4,5,5,6,6,6-nonafluoro-1-hexanethiolate.

In some embodiments, as described elsewhere herein, a sensing element comprises a polymer. The polymer may serve as a matrix in which one or more other components are disposed (e.g., carbon black and any species grafted thereto). In some embodiments, the polymer has a chemical composition such that one or more analytes may interact strongly therewith. The chemical composition of the polymer may be such that other, different, analytes do not interact strongly therewith or do not interact therewith to an appreciable degree. As described above, this may allow for the sensing element to have different interactions with different analytes, and so for it to be able to distinguish different analytes from each other. When a sensing element comprises a polymer including two or more types of monomers (e.g., a copolymer, a terpolymer, etc.), the different types of monomers may be configured to respond similarly to a variety of analytes (e.g., the different types of monomers may respond strongly to one set of analytes and weakly to another), may be configured to respond similarly to some analytes and differently to others (e.g., the sets of analytes to which the different types of monomers respond strongly may partially but not completely overlap, the sets of analytes to which the different types of monomers respond weakly may partially but not completely overlap), or may be configured to respond differently to analytes (e.g., the sets of analytes to which the different types of monomers respond strongly do not overlap, the sets of analytes to which the different monomers respond weakly do not overlap).

A variety of suitable polymers may be employed in the sensing elements described herein. The sensing element may comprise polymers that are amorphous, crystalline, and/or microcrystalline (e.g., in some embodiments, a sensing element comprises a polymer that is partially amorphous and partially microcrystalline). The sensing element may comprise a synthetic polymer, a natural polymer, and/or a modified natural polymer (e.g., a natural polymer that has undergone one or more chemical reactions that have resulted in a structural change). The sensing element may comprise polymers that are polar, apolar, and/or amphiphilic.

Non-limiting examples of suitable types of polymers include poly(ester)s, poly(acid)s, poly(alcohol)s, poly(silane)s, poly(siloxanes), poly(thiophene)s, poly(sulfone)s, poly(amine)s, poly(amide)s, poly(ether)s, poly(nitrile)s, poly(aromatic)s, halogenated polymers (e.g., halogenated poly(aromatic)s, halogenated poly(aliphatic)s), poly(heteroaromatic)s, acrylics, poly(carbonate)s, poly(imide)s, derivatives of cellulose, and copolymers (e.g., poly(aromatic-co-acid)s, poly(aliphatic-co-acid)s).

Non-limiting examples of suitable polymers include poly(ethylene adipate), poly(methyl methacrylate), poly(bisphenol A carbonate), poly(acrylic acid), poly(vinylidene chloride-co-acrylonitrile), poly(ethylene acrylic acid), ethyl cellulose, hydroxypropyl cellulose, poly(dimethylsiloxane-co-diphenylsiloxane), poly(dimethylsiloxane-co-alkylmethylsiloxane), poly(3,4,-ethylenedioxythiophene), poly(3-hexylthiophene-2,5-diyl), poly(N-vinyl pyrrolidone), poly(ethylene glycol), poly(styrene-co-acrylonitrile), poly(styrene), poly(4-methylstyrene), poly(styrene-co-methylstyrene), poly(vinylbenzylchloride), poly(4-fluorostyrene), poly(4-chlorostyrene), poly(4-vinylpyridine), poly(2-vinylpyridine), poly(styrene-co-maleic acid), poly(methylvinylether-co-maleic acid), poly(aniline), matrimid, poly(4-vinylphenol), and poly(epichlorohydrin).

A sensing element may comprise a polymer in a variety of suitable amounts. In some embodiments, a sensing element comprises both a plurality of gold nanoparticles and a polymer, and the ratio of the weight of the plurality of gold nanoparticles to the weight of the polymer is greater than or equal to 0.005, greater than or equal to 0.0075, greater than or equal to 0.01, greater than or equal to 0.02, greater than or equal to 0.03, greater than or equal to 0.04, or greater than or equal to 0.05. In some embodiments, a sensing element comprises both a plurality of gold nanoparticles and a polymer, and the ratio of the weight of the plurality of gold nanoparticles to the weight of the polymer is less than or equal to 0.06, less than or equal to 0.05, less than or equal to 0.04, less than or equal to 0.03, less than or equal to 0.02, less than or equal to 0.01, or less than or equal to 0.0075. Combinations of the above-referenced ranges are also possible (e.g., greater than or equal to 0.005 and less than or equal to 0.06). Other ranges are also possible.

The sensing element may further comprise one or more additional components. For instance, the sensing element may further comprise a surfactant and/or a residual solvent (e.g., a solvent from which the sensing element was formed but that did not fully evaporate). The sensing element may comprise a variety of surfactants, such as anionic surfactants (e.g., a surfactant comprising a sulfonate functional group, a surfactant comprising a deprotonated acidic group), cationic surfactants (e.g., a surfactant comprising a quaternary amine functional group), and/or neutral surfactants. In some embodiments, a sensing element comprises a surfactant comprising an alkyl group. Some suitable surfactants may be small molecules (e.g., molecules having a molecular weight of less than or equal to 500 g/mol, such as molecules having a molecular weight of between 300 g/mol and 500 g/mol), some suitable surfactants may be oligomers (e.g., molecules having a molecular weight of greater than or equal to 500 g/mol and less than or equal to 900 g/mol), and some suitable surfactants may be polymers. For instance, one or more of the polymers described above that exhibits surfactant behavior may be included in a sensing element.

When a sensing element comprises additional components, the additional components typically make up a relatively small portion thereof. For instance, the additional components may make up less than or equal to 10 wt %, less than or equal to 7.5 wt %, less than or equal to 5 wt %, less than or equal to 2 wt %, less than or equal to 1 wt %, less than or equal to 0.75 wt %, less than or equal to 0.5 wt %, less than or equal to 0.2 wt %, or less than or equal to 0.1 wt % of a sensing element. In some embodiments, the additional components make up greater than or equal to 0 wt %, greater than or equal to 0.1 wt %, greater than or equal to 0.2 wt %, greater than or equal to 0.5 wt %, greater than or equal to 0.75 wt %, greater than or equal to 1 wt %, greater than or equal to 2 wt %, greater than or equal to 5 wt %, or greater than or equal to 7.5 wt % of a sensing element.

In some embodiments, a sensing element does not include any additional components. Combinations of the above-referenced ranges are also possible (e.g., less than or equal to 10 wt % and greater than or equal to 0 wt %). Other ranges are also possible. In some embodiments, an additional component is present in a sensing element in one or more of the ranges listed above. In some embodiments, a sensing element comprises two or more additional components, and each additional component may be independently present in the sensing element in one or more of the ranges listed above. In some embodiments, a sensing element comprises two or more additional components, and all of the additional components together are present in one or more of the ranges listed above.

Figure 6D:
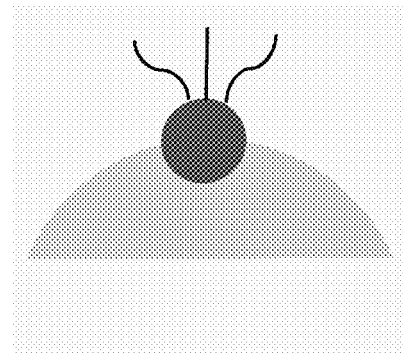
FIG. 6d illustrates carbon black grafted with ligand-attached gold nanoparticles embedded in a polymer matrix, in accordance with some embodiments.
Figure 7A:
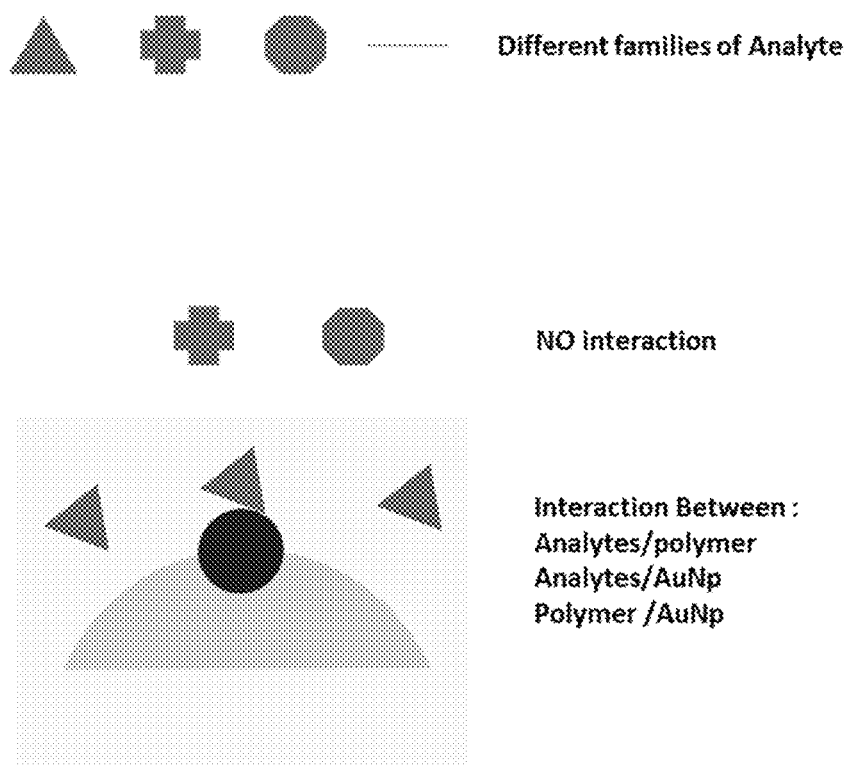
FIG. 7a illustrates the interactions present in a mixture of carbon black grafted with gold nanoparticles embedded in a polymer matrix with some analytes, in accordance with some embodiments.
Figure 7B:
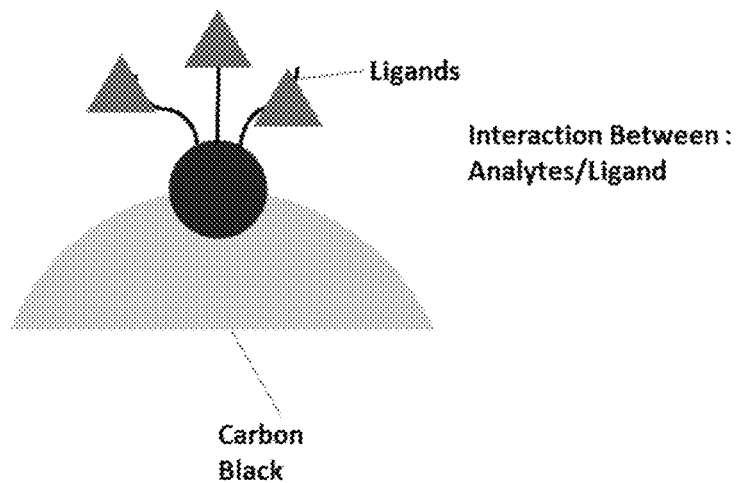
FIG. 7b illustrates the interactions present in a mixture of carbon black grafted with ligand attached gold nanoparticles with some analytes, in accordance with some embodiments.
Figure 7C:
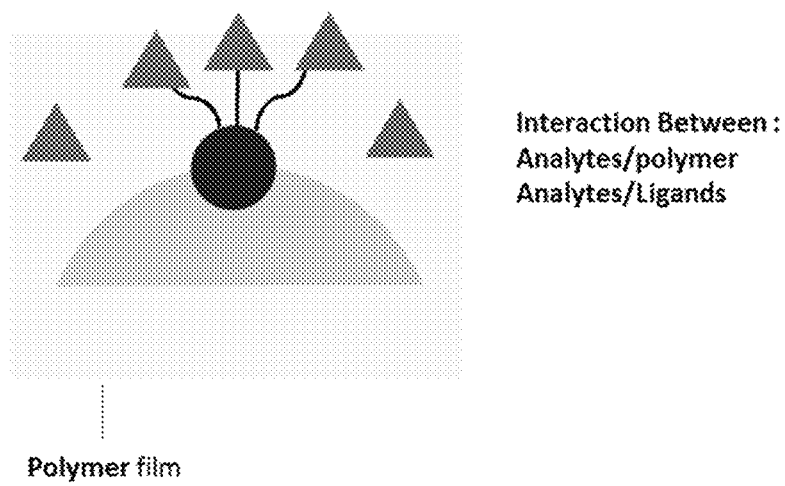
FIG. 7c illustrates the interactions present in a mixture of carbon black grafted with ligand-attached gold nanoparticles embedded in a polymer matrix with some analytes, in accordance with some embodiments.

As described above, in some embodiments, the sensing material (e.g., one or more component(s) of a sensing element) could be CB-AuNp, a polymer, a ligand, or a surfactant, or a mixture of two or more of these components (FIGS. 6a, 6b, 6b, 6d). In some embodiments, as described above, the sensing element is configured to respond to one or more analytes. The sensing materials could be considered as a binding site for the exposed analyte or mixture of analytes (FIG. 7a). In other words, in some embodiments, a sensing element interacts with an analyte and/or a mixture of analytes by binding. The binding may be covalent bonding, dipole-dipole interactions, van der Waals bonding, hydrogen bonding, and/or ionic bonding. Further possible methods of interaction between an analyte and the sensing element include absorption and adsorption. In some embodiments, an analyte interacts with a sensing element in one or more of the above-referenced manners (e.g., by both dipole-dipole interactions and absorption). Without wishing to be bound by any particular theory, it is believed that more binding sites available within a sensing element may create more interaction with an analyte or mixture of analytes (FIGS. 7b, 7c), which may then lead to a larger change in the electrical response.

The sensing elements described herein may be suitable for sensing a variety of analytes. In some embodiments, a sensing element may be suitable for sensing a fluid analyte and/or an analyte dispersed in a fluid. The fluid may be a gas. For instance, in some embodiments, a sensing element is configured to sense an analyte that is a gas and/or configured to sense an analyte other than a gas that is dispersed in a gas (e.g., a liquid dispersed in a gas, a solid dispersed in a gas). The analyte may be a liquid with a relatively high vapor pressure (e.g., a volatile organic compound).

In some embodiments, a sensing element is configured to sense an analyte that is an organic compound, such as an organic solvent. Non-limiting examples of suitable organic compounds and/or solvents include those comprising a ketone functional group (e.g., acetone), those comprising an alcohol functional group (e.g., ethanol), those comprising an organic acid functional group, those comprising an amine functional group, those comprising an aromatic functional group, those comprising an ether functional group, those comprising an ester functional group, those comprising an aldehyde functional group, those comprising an $NO_x$ functional group, those comprising a $SO_x$ functional group, those comprising an alkane functional group, and/or those comprising an alkene functional group. In some embodiments, a sensing element is configured to sense an inorganic compound, such as an inorganic acid.

It should also be understood that some sensors may be configured to sense two or more analytes. By way of example, some sensors may be configured to sense complex smells (e.g., a plurality of analytes, such as a plurality of analytes being present in particular relative amounts). In some embodiments, a sensing element is configured to sense a particular analyte and comprises one or more components that enhance its sensitivity to that analyte. The relevant component(s) may be complementary to the analyte (e.g., may configured to undergo a chemical reaction with the analyte, such as an acid-base reaction) or may be chemically similar to the analyte (e.g., may be configured to dissolve the analyte therein). By way of example, in some embodiments, a sensing element configured to sense an analyte comprising an acid functional group comprises one or more base functional groups (e.g., a polymer and/or a ligand comprising one or more base functional groups, such as a polymer and/or a ligand comprising one or more amine groups). As another example, a sensing element configured to sense an analyte comprising an aromatic compound comprises one or more aromatic functional groups (e.g., a polymer and/or a ligand comprising one or more aromatic functional groups).

A sensor comprising a sensing element may be configured to output a signal that varies based on the amount and/or type of analyte the sensing element is exposed to. For instance, in some embodiments, a sensing element is configured to undergo a change in one or more properties (e.g., electrical resistivity, thickness) upon exposure to an analyte. The sensing element may output a signal based on one or more of these changes. As described above, the magnitude of the change in the property or properties may vary based on the identity of the analyte (e.g., the chemical composition of the analyte), the amount of analyte to which the sensing element is exposed (e.g., the concentration of the analyte in a fluid to which the sensing element is exposed), and the amount of time for which the sensing element is exposed to the analyte. In some embodiments, the magnitude of the change in the property or properties may indicate an amount of binding between the analyte and one or more components of the sensing element. By way of example, a larger change in the property or properties may indicate a larger amount of binding between an analyte and one or more components of the sensing element and a smaller change in the property or properties may indicate a smaller amount of binding between the analyte and the components of the sensing element.

In some embodiments, a plurality of sensors comprises two or more sensors to respond differently to analytes (e.g., two or more sensors configured to output different signals in response to the same analyte).

In some embodiments, a sensing element is configured to undergo a change in electrical resistivity of greater than or equal to 0.1%, greater than or equal to 0.2%, greater than or equal to 0.5%, greater than or equal to 0.75%, greater than or equal to 1%, greater than or equal to 2%, greater than or equal to 5%, greater than or equal to 7.5%, greater than or equal to 10%, greater than or equal to 20%, greater than or equal to 50%, greater than or equal to 75%, greater than or equal to 100%, greater than or equal to 200%, or greater than or equal to 500% upon exposure to an analyte or combination of analytes. In some embodiments, a sensing element is configured to undergo a change in electrical resistivity of less than or equal to 800%, less than or equal to 500%, less than or equal to 200%, less than or equal to 100%, less than or equal to 75%, less than or equal to 50%, less than or equal to 20%, less than or equal to 10%, less than or equal to 7.5%, less than or equal to 5%, less than or equal to 2%, less than or equal to 1%, less than or equal to 0.75%, less than or equal to 0.5%, or less than or equal to 0.2% upon exposure to an analyte or combination of analytes. Combinations of the above-referenced ranges are also possible (e.g., greater than or equal to 0.1% and less than or equal to 800%). Other ranges are also possible.

It should be understood that the above-referenced ranges may refer to the response of a sensing element to a single analyte (e.g., in the presence of one or more analytes, in the presence of no other analytes, in the presence of a fluid) or may refer to the response of a sensing element to a combination of analytes (e.g., in the presence of one or more other analytes, in the presence of no other analytes, in the presence of a fluid). It should also be understood that the above-referenced ranges may refer to the response of a sensing element at a variety of points in time (e.g., immediately upon exposure to the analyte, after exposure for a defined period of time, after achieving a steady state response to the analyte).

The electrical resistivity of the sensing elements described herein may be a variety of suitable values when not exposed to any analytes. In some embodiments, a sensing element may have a resistivity of approximately 100 kilohms (e.g., between 50 and 150 kilohms) when not exposed to any analytes.

The sensing elements described herein may have a variety of suitable thicknesess. In some embodiments, a sensing element has a thickness of greater than or equal to 1 micron, greater than or equal to 1.5 microns, greater than or equal to 2 microns, greater than or equal to 2.5 microns, greater than or equal to 3 microns, greater than or equal to 4 microns, greater than or equal to 5 microns, greater than or equal to 7.5 microns, greater than or equal to 10 microns, or greater than or equal to 12.5 microns. In some embodiments, a sensing element has a thickness of less than or equal to 15 microns, less than or equal to 12.5 microns, less than or equal to 10 microns, less than or equal to 7.5 microns, less than or equal to 5 microns, less than or equal to 4 microns, less than or equal to 3 microns, less than or equal to 2.5 microns, less than or equal to 2 microns, or less than or equal to 1.5 microns. Combinations of the above-referenced ranges are also possible (e.g., greater than or equal to 1 micron and less than or equal to 15 microns). Other ranges are also possible. It should also be understood that the above-referenced ranges may refer to sensing elements prior to exposure to any analytes, during exposure to one or more analytes, and/or after exposure to one or more analytes.

As described above, carbon black (CB) may be used in combination with gold nanoparticles (AuNp or AuNps), such as gold nanoparticles with sizes ranging between 2-50 nm to serve as the conductive material. CB/AuNp proportions could vary from 0.1 to 20 Wt % (weight %) of the gold mass content, or may be present in other relative amounts as described above. A variety of suitable methods may be employed to synthesize carbon black onto which a plurality of gold nanoparticles are grafted. By way of example, CB-AuNp could be synthesized in one or two consecutive steps of a chemical synthesis procedure which may involve elevating the process temperature or introducing ultrasound or both. The resulting CB-AuNp can improve sensitivity as it creates new binding sites for analytes on the CB.

To further improve sensitivity, and as also described above, CB-AuNp could be modified with various thio-carbon derivative ligands, which may contain various organic substituents such as acid, ester, amine, thiol, alcohol, aldehydes or aromatics (FIGS. 6b, 6d) to produce CB-AuNp-L.

CB-AuNp-L can be synthesized directly with CB or after the formation of CB-AuNp, or by any other suitable method. In the case of adding polymers and/or surfactants to the sensing material, CB-AuNp-L can be synthesized before or after the addition. To realize an effective thin film composite sensor, the CB-AuNp or CB-AuNp-L are typically dispersed in a host solvent and/or surfactant combination. Additionally, other methods of forming sensors and sensing elements are also contemplated and have been described elsewhere herein. Various surfactants such as anionic, cationic and neutral surfactants at different concentrations could be used for effective dispersion in some embodiments. While the addition of the surfactant is believed to promote better dispersion, it can however be optimized to increase the sensitivity as well in some embodiments. It can also be appreciated that some surfactants are polymer based and could be used to increase the binding sites, thereby increasing the sensitivity.

With respect to the host solvent, various solvent or mixture of solvents such as polar, apolar, organic and/or aqueous can be used. Without wishing to be bound by any particular theory, it is believed that the nature of the solvent can have an impact on the quality of the thin film composite, and thereby affect the sensitivity of the resultant sensing element. Often a chemically-sensitive polymer base is used in the composite formulation. Various polymers such as polystyrene, polyamine, polyacid, polyols, polyesters, polysiloxanes, polyaromatic, cellulose derivatives, polyethylene, polyethylene glycol and their derivatives, and conductive polymers can be used.

The following description is presented to illustrate a specific example to enable the reproduction of the synthesis of the composite formulation with CB-AuNp-L, but not used to limit the scope of the following.

EXAMPLE 1

This Example describes an exemplary procedure for synthesizing carbon black onto which a plurality of gold nanoparticles is grafted.

The following procedure may be employed to synthesize a plurality of gold nanoparticles grafted onto carbon black.
A) CB-AuNp Synthesis Procedure
1) $HAuCl_4$ is mixed with carbon black (CB) with the desired amount of weight, from 0.1 to 20 wt % depending on necessity and/or other factors.
2) Solvent is added to the mixture and the mixture is allowed to disperse well at room temperature for 10 minutes.
3) After the reaction is cooled down, a reducing agent ($NaBH_4$) is added at 0° C.
4) The solution is stirred for anywhere from 1 hour to 2 days depending on necessity and/or other factors.
5) The dispersed solution is filtered using a filter paper and washed multiples times with a solvent.
6) The resulting solid is dried at 130° C. from anywhere between 3 to 24 hours depending on necessity.

EXAMPLE 2

This Example describes an exemplary procedure for synthesizing carbon black onto which a plurality of gold nanoparticles is grafted and for which a plurality of ligands are grafted onto the gold nanoparticles.

The following procedure may be employed to synthesize a plurality of gold nanoparticles grafted onto carbon black and a plurality of ligands grafted onto the gold nanoparticles.
B) CB-AuNp-L Synthesis Procedure 1) 100-200 mg of the solid CB-AuNp prepared above (i.e., as described in Example 1) is dispersed in a solvent and mixed for 10 minutes.
2) 2 to 20 molar equivalents of thio-derivative ligand were added.
3) The solution is stirred for anywhere from 1 hour to 2 days depending on necessity and/or other factors.
4) The dispersed solution is filtered using a filter paper and washed multiples times with a solvent.
5) The resulting solid is dried at 130° C. from anywhere between 3 to 24 hours depending on necessity and/or other factors.

EXAMPLE 3

This Example describes an exemplary procedure for fabricating a solution that may be deposited to form a sensing element comprising carbon black onto which a plurality of gold nanoparticles are grafted, and for which a plurality of ligands are optionally grafted onto the gold nanoparticles.

The following procedure may be employed to fabricate a solution comprising carbon black onto which a plurality of gold nanoparticles is grafted (and, optionally, for which a plurality of ligands are grafted onto the gold nanoparticles).

C) Composite Solution Preparation
1) CB-AuNp or CB-AuNp-L, surfactant, solvent and/or polymer are mixed together in an optimal ratio, depending on necessity.
2) The mixture is then dispersed well with ultrasonic bath from anywhere between 30 minutes to 6 hours depending on necessity and/or other factors.
3) The well dispersed colloid is kept at room temperature for 20 minutes.
4) The resulting colloidal solution is ready for deposition on to a substrate.

Results:

The following examples shall be only used to illustrate two specific embodiments of an increase in sensitivity and selectivity with CB-AuNp and CB-AuNp-L based composites. It should be apparent to those skilled in the art that changes and modifications may be made to these examples without departing from the principles discussed herein.

EXAMPLE 4

This Example describes the fabrication and testing of sensing elements comprising carbon black onto which a plurality of gold nanoparticles are grafted, a polymer, and a surfactant. This Example compares these sensing elements to sensing elements lacking the plurality of gold nanoparticles.

Figure 8A:
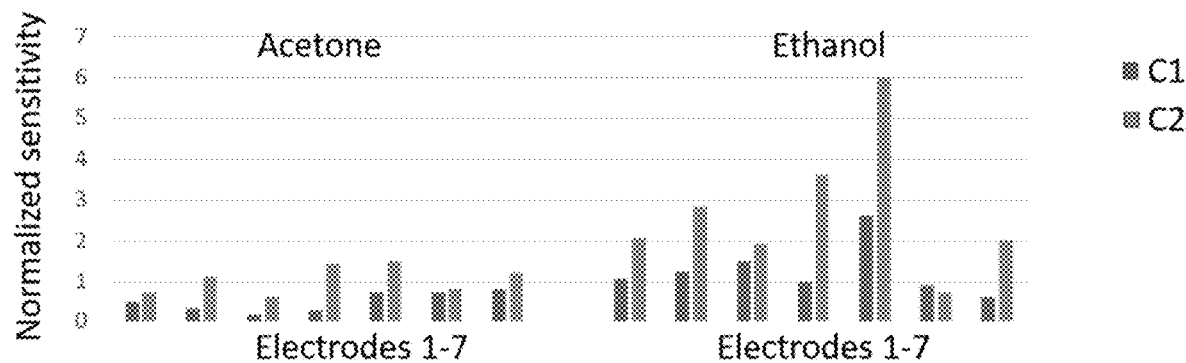
FIG. 8a is a graph representing the difference of sensitivity in % for C1 (sensor containing carbon black, surfactant and solvent) and C2 (sensor containing gold nanoparticles grafted carbon black, surfactant and solvent) for the same concentration of acetone and ethanol, in accordance with some embodiments.

Two sensors were fabricated on a substrate. One of them used a composite (C1) containing CB, Polymer (P1), surfactant (S1) and solvent (Sol1). In other words, C1 was fabricated by depositing a solution comprising CB, P1, S1, and Sol1 onto the substrate. The resulting sensing element included CB, P1, S1, and residual amounts of Sol1 not evaporated away after deposition of the solution. The second composite (C2) contained CB-AuNp, P1, S1 and Sol1. In other words, C2 was fabricated by depositing a solution comprising CB-AuNP, P1, S1, and Sol1 onto the substrate. The resulting sensing element included CB-AuNP, S1, and residual amounts of Sol1 not evaporated away after deposition of the solution. The composites were optimized to increase sensitivity for two analytes, namely acetone and ethanol. They were also optimized to be more selective for ethanol. The solutions employed to form composites C1 and C2 were deposited on 7 electrodes each, S1 was allowed to evaporate from each composite, and then the composites were exposed to acetone and ethanol. FIG. 8a shows the response of C1 and C2 for both the analytes across the 7 electrodes. It can be clearly seen that C2 has a higher sensitivity than C1 and that in general both composite systems have higher selectivity to ethanol.

EXAMPLE 5

This Example describes the fabrication and testing of sensing elements comprising carbon black onto which a plurality of gold nanoparticles are grafted, a plurality of ligands grafted onto the gold nanoparticles, a polymer, and a surfactant. This Example compares these sensing elements to sensing elements lacking the plurality of gold nanoparticles.

Figure 8B:
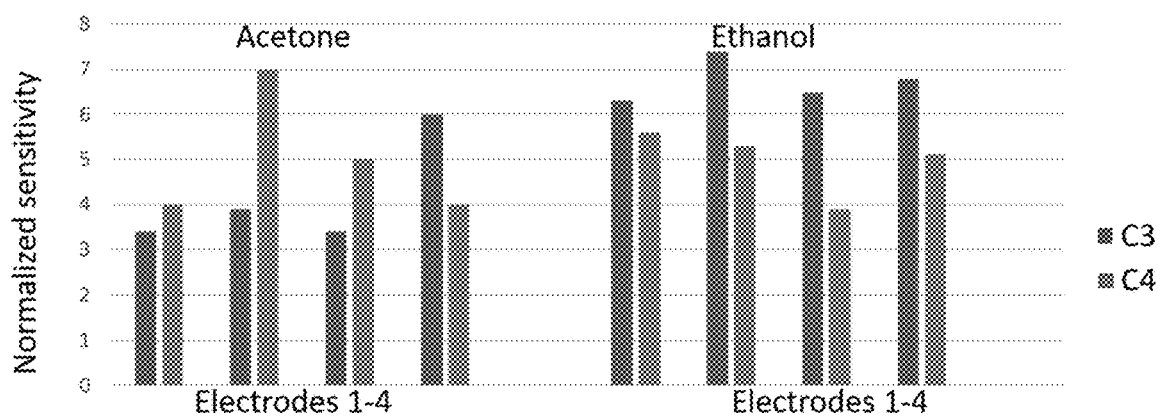
FIG. 8b is a graph representing the difference of sensitivity in % for C3 (sensor containing carbon black, polymer, surfactant and solvent) and C4 (sensor containing gold nanoparticles grafted carbon black, ligand, surfactant and solvent) for the same concentration of acetone and ethanol, in accordance with some embodiments.

Two sensors were fabricated on a substrate. The first used a composite (C3) containing CB, Polymer (P1), surfactant (S1) and solvent (Sol1). In other words, C3 was fabricated by depositing a solution comprising CB, P2, S1, and Sol1 onto the substrate. The resulting sensing element included CB, P1, S1, and residual amounts of Sol1 not evaporated away after deposition of the solution. The second composite (C4) contained CB-AuNp-L, P1, S1 and Sol1. C4 was optimized for increased selectivity for Acetone. In other words, C4 was fabricated by depositing a solution comprising CB-AuNp-L, P1, S1, and Sol1 onto the substrate. The resulting sensing element included CB-AuNP-L, P1, S1, and residual amounts of Sol1 not evaporated away after deposition of the solution. Composites C3 and C4 were deposited on 4 electrodes each, S1 was allowed to evaporate from each composite, and then the composites were exposed to acetone and ethanol. FIG. 8b shows the response of C3 and C4 for both the analytes across the 4 electrodes. It can be clearly seen that C4 has higher selectivity to acetone than C3.

Paragraph 1. Carbon black grafted with gold nanoparticles sized between 2-50 nm as a sensing material for improved chemical sensitivity and selectivity.
  Carbon black and gold nanoparticles weight proportions can vary from 0.1 to 20 Wt % of gold content.
  Carbon black grafted with gold nanoparticles can be synthesized in one or multiple steps synthesis with either high temperature or ultrasound or both.

Paragraph 2. Carbon black grafted with ligand attached gold nanoparticles sized between 2-50 nm as a sensing material for improved chemical sensitivity and selectivity.
  Gold nanoparticles could be modified with different thio-carbon derivative ligands, containing various substituents such as acid, ester, amine, thiol, alcohol, aldehydes or aromatics.
  Gold nanoparticles modification by thio-carbon derivatives can be done before or after the formation of gold nanoparticle grafted carbon black.
  Gold nanoparticles modification by thio-carbon derivatives can be done before or after the addition of a polymer and/or surfactant.
  Various surfactants such as anionic, cationic or neutral can be used for the formulation
Various solvent or mixture of solvents such as polar, apolar, organic or aqueous can be used for the formulation.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A sensor comprising:
    a sensing element comprising a polymer, carbon black, and gold nanoparticles grafted onto the carbon black, wherein the gold nanoparticles grafted onto the carbon black are attached thereto via chemical bonds, a ratio of a weight of the gold nanoparticles to a weight of the carbon black is greater than or equal to 0.25 and less than or equal to 0.5, and a ratio of the weight of the gold nanoparticles to a weight of the polymer is greater than or equal to 0.005 and less than or equal to 0.02; and
    a plurality of electrodes electrically coupled to the sensing element, the plurality of electrodes configured to sense a change in a resistivity of the sensing element upon exposure to an analyte.

2. The sensor of claim 1, wherein the sensing element further comprises:
    a plurality of ligands grafted onto the gold nanoparticles.

3. The sensor of claim 2, wherein the plurality of ligands comprises a thiolate functional group.

4. The sensor of claim 2, wherein the plurality of ligands comprises an amine functional group.

5. The sensor of claim 2, wherein the plurality of ligands comprises an aromatic functional group.

6. The sensor of claim 2, wherein the plurality of ligands comprises a fluorinated functional group.

7. The sensor of claim 2, wherein the plurality of ligands grafted onto the gold nanoparticles are attached thereto via chemical bonds.

8. The sensor of claim 1, wherein an average diameter of the gold nanoparticles is greater than or equal to 2 nm and less than or equal to 50 nm.

9. The sensor of claim 1, wherein the polymer comprises two or more types of monomers.

10. The sensor of claim 1, wherein the sensing element further comprises one or more additional components, and wherein the one or more additional components make up less than or equal to 10 wt % of the sensing element.

11. The sensor of claim 10, wherein the one or more additional components comprise a surfactant.

12. The sensor of claim 1, wherein the analyte is a gas and/or a vapor.

13. The sensor of claim 1, wherein the analyte is an organic compound.

14. The sensor of claim 1, wherein the carbon black takes the form of a plurality of particles comprising carbon black.

15. The sensor of claim 1, wherein the polymer includes one or more of poly(ethylene adipate), poly(methyl methacrylate), poly(bisphenol A carbonate), poly(acrylic acid), poly(vinylidene chloride-co-acrylonitrile), poly(ethylene acrylic acid), ethyl cellulose, hydroxypropyl cellulose, poly(dimethylsiloxane-co-diphenylsiloxane), poly(dimethylsiloxane-co-alkylmethylsiloxane), poly(3,4,-ethylenedioxythiophene), poly(3-hexylthiophene-2,5-diyl), poly(N-vinyl pyrrolidone), poly(ethylene glycol), poly(styrene-co-acrylonitrile), poly(styrene), poly(-methyl styrene), poly(styrene-co-methyl styrene), poly(vinylbenzylchloride), poly(4-fluorostyrene), poly(-chlorostyrene), poly(-vinylpyridine), poly(-vinylpyridine), poly(styrene-co-maleic acid), poly(methylvinylether-co-maleic acid), poly(aniline), matrimid, poly(-vinylphenol), and poly(epichlorohydrin).

16. A plurality of sensors comprising the sensor of claim 1.

17. The plurality of sensors of claim 16, wherein the plurality of sensors are positioned in a repeating lattice structure.

18. The plurality of sensors of claim 17, wherein the repeating lattice structure is a rectangular lattice.

19. The plurality of sensors of claim 17, wherein the repeating lattice structure is a square lattice.

20. The sensor of claim 1, wherein the carbon black and the gold nanoparticles are dispersed in a matrix formed by the polymer.

* * * * *